United States Patent [19]

Hotten et al.

[11] Patent Number: 4,963,558
[45] Date of Patent: Oct. 16, 1990

[54] PYRAZOLO-[3,4-G]ISOQUINOLINE DERIVATIVES USEFUL TO TREAT CNS DISORDERS

[75] Inventors: Terrence M. Hotten, Farnborough Hants; Graham H. Timms, Surrey; David E. Tupper, Berks, all of England

[73] Assignee: Lilly Industries Limited, Basingstoke, England

[21] Appl. No.: 447,319

[22] Filed: Dec. 7, 1989

[30] Foreign Application Priority Data

Dec. 8, 1988 [GB] United Kingdom ................ 8828669

[51] Int. Cl.⁵ .................... A61K 31/47; C07D 489/04
[52] U.S. Cl. ........................................ 514/293; 546/82
[58] Field of Search ........................... 546/82; 514/293

[56] References Cited

U.S. PATENT DOCUMENTS

| | | | |
|---|---|---|---|
| 4,230,861 | 10/1980 | Kornfeld et al. | 546/82 |
| 4,468,401 | 8/1984 | Hahn | 546/82 |
| 4,596,871 | 6/1986 | Schaus et al. | 546/82 |
| 4,762,843 | 8/1988 | Caprathe et al. | 514/293 |

Primary Examiner—Mary C. Lee
Assistant Examiner—L. A. Mittenberger
Attorney, Agent, or Firm—Robert A. Conrad; Leroy Whitaker

[57] ABSTRACT

Pharmaceutical compounds of the formula

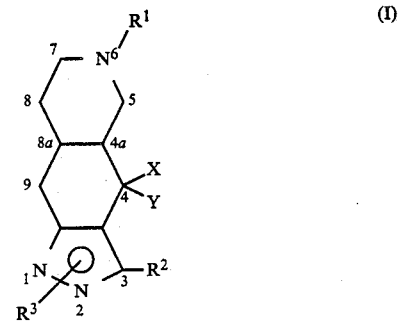

(I)

in which $R^1$ is hydrogen or $C_{1-6}$ alkyl, $R^2$ is hydrogen, $C_{1-6}$ alkyl optionally substituted by $C_{3-9}$ cycloalkyl or optionally substituted phenyl, $C_{3-9}$ cycloalkyl, optionally substituted phenyl, or —$SR^4$ where $R^4$ is $C_{1-6}$ alkyl optionally substituted by $C_{3-9}$ cycloalkyl or optionally substituted phenyl, or $C_{3-9}$ cycloalkyl, $R^3$ is hydrogen, $C_{1-6}$ alkyl optionally substituted by $C_{3-9}$ cycloalkyl or optionally substituted phenyl, $c_{3-9}$ cycloalkyl, or optionally phenyl, and either X and Y are both hydrogen or together are =O; and acid addition salts thereof. These compounds show useful effects on the central nervous system.

7 Claims, No Drawings

PYRAZOLO-[3,4-G]ISOQUINOLINE DERIVATIVES USEFUL TO TREAT CNS DISORDERS

This invention relates to organic compounds and their use as pharmaceuticals.

The compounds of the invention are of the formula

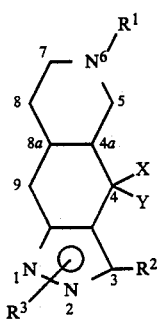

(I)

in which $R^1$ is hydrogen or $C_{1-6}$ alkyl, $R^2$ is hydrogen, $C_{1-6}$ alkyl optionally substituted by $C_{3-9}$ cycloalkyl or optionally substituted phenyl, $C_{3-9}$ cycloalkyl, optionally substituted phenyl, or $-SR^4$ where $R^4$ is $C_{1-6}$ alkyl optionally substituted by $C_{3-9}$ cycloalkyl or optionally substituted phenyl, or $C_{3-9}$ cycloalkyl, $R^3$ is hydrogen, $C_{1-6}$ alkyl optionally substituted by $C_{3-9}$ cycloalkyl or optionally substituted phenyl, $C_{3-9}$ cycloalkyl, or optionally substituted phenyl, and either X and Y are both hydrogen or together are =O; and acid addition salts thereof. These compounds show useful effects on the central nervous system.

When reference is made to $C_{1-6}$ alkyl, the alkyl group can be straight or branched chain and examples include methyl, ethyl, propyl, isopropyl, butyl and tert. butyl. Preferred alkyl groups contain 1 to 4 carbon atoms, and methyl and ethyl are especially preferred. A $C_{3-9}$ cycloalkyl group includes for example cyclopropyl, cyclopentyl and cyclohexyl and these groups substituted by one or more, such as one or two, methyl or ethyl redical. The most preferred cycloalkyl group is cyploroyl. When one of the groups is optionally substituted phenyl it can be phenyl or phenyl substituted by 1 to 3 substituents selected from $C_{1-4}$ alkyl especially methyl, $C_{1-4}$ alkoxy especially methoxy and ethoxy, hydroxy, nitro, cyano, halo especially chloro and bromo, trifluoromethyl, carboxyl, tetrazolyl and carboxamide.

Preferred values of $R^1$ are hydrogen and $C_{1-4}$ alkyl, especially methyl and ethyl. Preferred values of $R^2$ are hydrogen, $C_{1-4}$ alkyl and $C_{3-9}$ cycloalkyl, and preferred values of $R^4$ are $C_{1-4}$ alkyl. Preferred values of $R^3$ are hydrogen and $C_{1-4}$ alkyl. It is preferred that X and Y are both hydrogen.

The compounds of the invention are useful both in their free base and acid addition salt forms. The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, nicotinic or isonicotinic acid, or organic sulphonic acids for example methane sulphonic, ethane sulphonic, 2-hydroxyethane sulphonic, toluene-p-sulphonic, or naphthalene-2-sulphonic acid. Apart from pharmaceutically acceptable acid addition salts, other salts are also included within the scope of acid addition salts such as, for example, those with picric or oxalic acids; they may serve as intermediates in the purification of the compounds or in the preparation of other, for example pharmaceutically acceptable, acid addition salts, or are useful for identification, characterisation or purification of the bases.

It will be appreciated that the compounds of formula (I) possess chiral centres at the 4a and 8a carbon atoms and accordingly stereoisomeric forms exist, that is, R,R; S,S; R,S and S,R forms. All such stereoisomers, and racemic mixtures of them, are included in this invention. Isomers can be isolated from racemic mixtures by conventional methods such as for the preparation of diastereoisomers followed by liberation of the enantiomers, or can be prepared by methods devised to give the pure isomer. The preferred enantiomer is the 4aR,8aR form.

A preferred group of compounds is of the formula

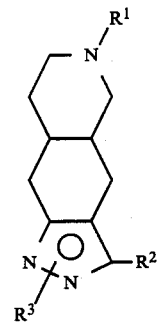

in which $R^1$ is $C_{1-4}$ alkyl, $R^2$ is $C_{1-4}$ alkyl optionally substituted by cyclopropyl, or $-SR^4$ where $R^4$ is $C_{1-4}$ alkyl, and $R^3$ is hydrogen; and acid addition salts thereof. It is preferred that the 4a,8a ring junction is trans.

Compounds of formula (I) above can be prepared by (a) reacting a compound of the formula

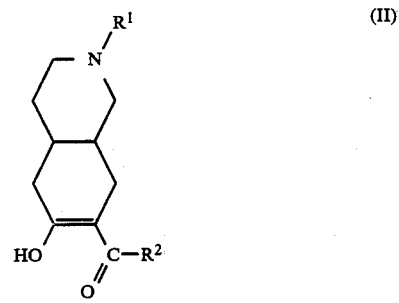

(II)

in which $R^1$ is hydrogen or $C_{1-6}$ alkyl and $R^2$ is hydrogen, $C_{1-6}$ alkyl optionally substituted by $C_{3-9}$ cycloalkyl or optionally substituted phenyl, $C_{3-9}$ cycloalkyl, or optionally substituted phenyl, with hydrazine or a hydrazine derivative of the formula $R^3NHNH_2$ (III) where $R^3$ is hydrogen, $C_{1-6}$ alkyl optionally substituted by $C_{3-9}$ cycloalkyl or optionally substituted phenyl, $C_{3-9}$ cycloalkyl, or optionally substituted phenyl: (b) reacting a compound of the formula

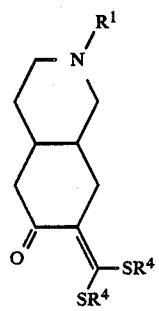

(IV)

in which $R^1$ is hydrogen or $C_{1-6}$ alkyl and $R^4$ is $C_{1-6}$ alkyl optionally substituted by cycloalkyl or optionally substituted phenyl, or $C_{3-9}$ cycloalkyl, with hydrazine or a hydrazine derivative of the formula $R^3NHNH_2$ where $R^3$ is as defined above; or (c) oxidising a compound of formula (I) in which X and Y are both hydrogen.

With regard to reaction (a), this is preferably carried out at a temperature of from 0° C. to 25° C. and in an inert organic solvent such as for example methanol. When $R^3$ is other than hydrogen a mixture of the 1- and 2-substituted products is obtained and separation of the individual isomers can be effected by conventional means such as chromatography or crystallisation.

Compounds of formula (II) can be prepared by acylation of a compound of the formula

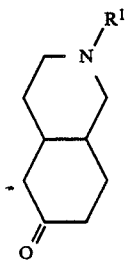

(V)

The acylation can be carried out, for example, by formation of an enamine by heating the compound in toluene with pyrrolidine or a similar base such as for example morpholine or piperidine, and acylation of the enamine thus formed using an acid chloride of formula $R^2COCl$ and triethylamine as base in an inert organic solvent such as for example dichloromethane at 0° C. to 25° C. Alternatively, the acylation can be effected by first forming the ketone enolate generated by means of a suitable base such as for example sodium hydride or potassium tert. butoxide, and then reacting the product with an ester of formula $R^2COOR$ where R is $C_{1-4}$ alkyl, in a suitable solvent such as for example tetrahydrofuran at a temperature of from 0° C. to 25° C.

The compounds of formula (V) can be prepared by hydrogenation of the enone:

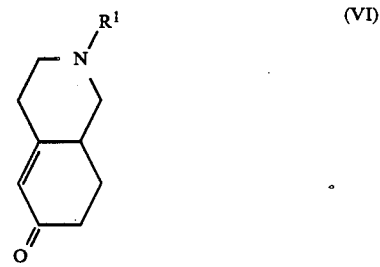

(VI)

Hydrogenation can be performed by a variety of methods. Catalytic hydrogenation using 10% palladium or charcoal in ethanol under pressure, typically gives a mixture of cis and trans isomers with regard to conformation of the hydrogen atoms at the 4a and 8a positions. The cis and trans isomers are racemic mixtures.

Hydrogenation can be effected by a different route employing lithium in ammonia with tetrahydrofuran as a cosolvent and using one mole of a suitable proton source, for example tert. butanol, to prevent over reduction to the alcohol. In this case the product is almost entirely a racemic mixture of the trans form.

The products of hydrogenation and the way in which the compounds of formula (I) in their various isomeric forms are derived from them, is summarised in the following Table:

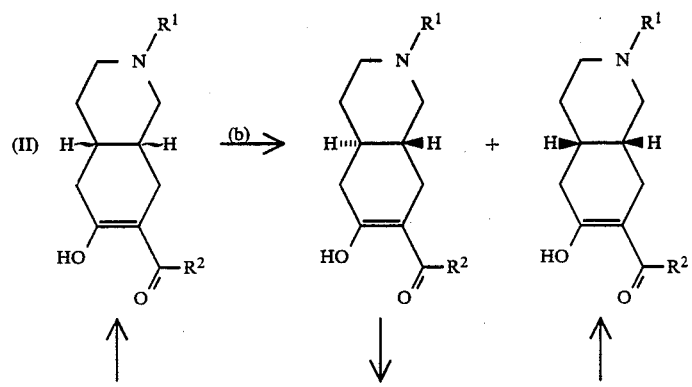

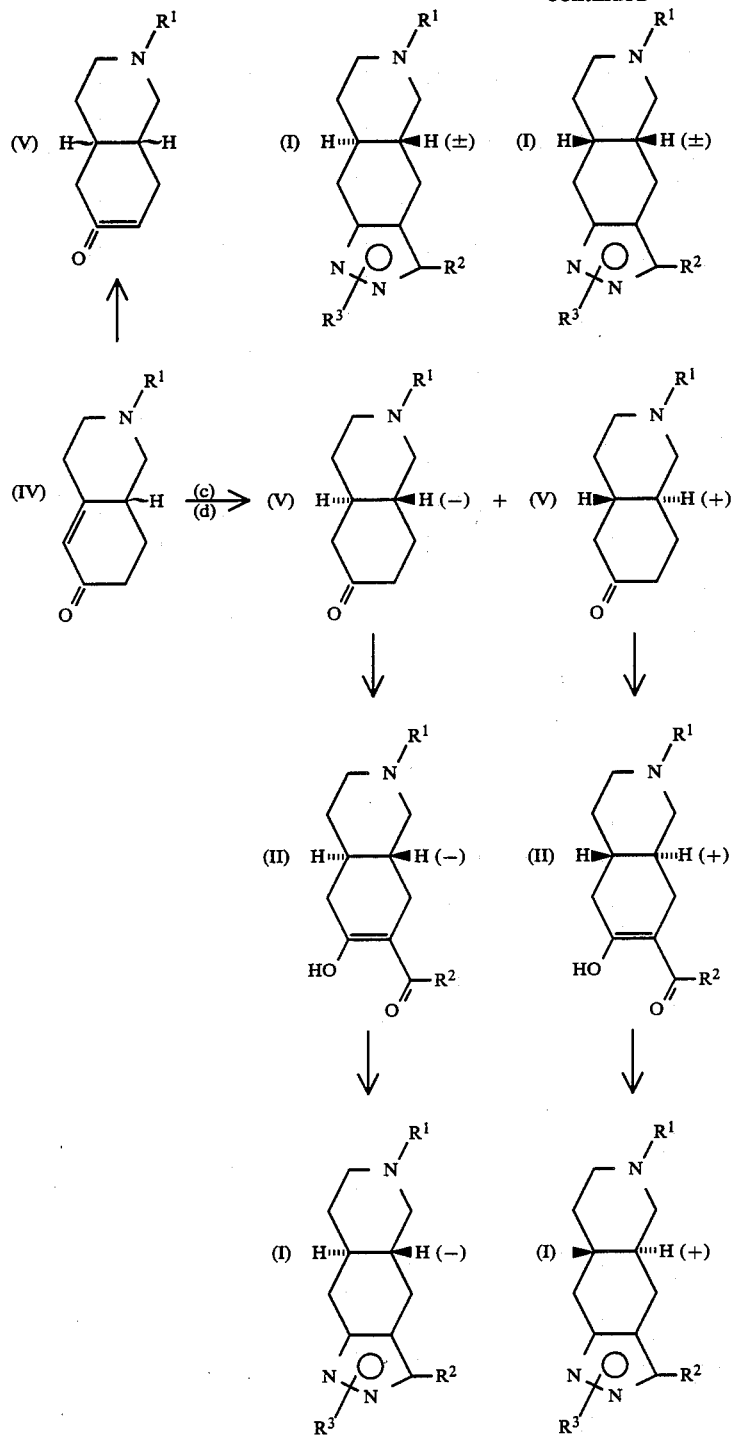

(a) catalytic hydrogenation with palladium and charcoal (b) separation of the trans and cis isomers by means of preparative HPLC (c) reduction of means of lithium in ammonia (d) separation of the trans ketone into its two enantiomers, for example, by crystallisation of the di-p-tolyl-L-tartaric acid salts.

The compounds of formula (VI) are known in the art, for example Marchant A. et. al., J. Chem. Soc. 1956, p. 327–331, and Durand-Henchoz S. et al., Bull. Soc. Chimique de France 1966, No. 11, p 3416–3422, and can be readily prepared by Robinson annalation of a compound such as

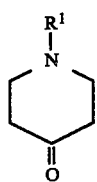

derived from an amine of formula R¹N(CH₂CH₂COOEt)₂. Hydrazine derivatives of formula R³NHNH₂ (III) are also known compoounds or can be made by methods well known in the art.

Compounds of formula (I) in which R² is —SR⁴ can be prepared from a compound of formula (IV), as indicated in step (b) of the process of the invention defined above. When R³ is other than hydrogen a mixture of the 1- and 2-substituted preducts is obtained and separation of the individual isomers can be effected by conventional means such as chromatography or crystallisation. The reaction is preferably performed at a temperature of from 0° C. to 25° C. and in an inert organic solvent such as for example methanol. Compounds of formula (IV) can be prepared from the appropriate compound of formula (V) by reaction of the ketone enolate generated by means of potassium tert. butoxide in tetrahydrofuran and carbon disulphide, followed by alkylation with a halide of formula R⁴I.

In order to obtain a compound of formula (I) in which X and Y together are =O, the corresponding compound in which X and Y are both hydrogen is oxidised. This reaction is preferably carried out at a temperature of from 0° C. to 80° C. and in an inert organic solvent such as for example acetic acid. The oxidising agent employed is preferably Jones reagent.

The compounds of the invention have useful central nervous system activity. They have low toxicity. This activity has been demonstrated in extensive testing in animal models using well-established procedures, such as the production of catalepsy, block of conditioned avoidance response and reversal of amphetamine-induced stereotyped behaviour in rats. The compounds of the invention, such as those in the following Examples, also block apomorphine-induced climbing in mice at dose levels of less than 200 mg/kg in the test described by Moore N. A. and Axton C. A., Psychopharmacology 1988, Vol. 94 p. 263. Specifically, the compounds of formula (I) and pharmaceutically-acceptable acid addition salts thereof, are potent centrally acting compounds with neuroleptic, sedative or relaxant or anti-emetic properties. These properties, coupled with their high therapeutic index, render them useful in the treatment of mild anxiety states and certain kinds of psychotic conditions such as schizophrenia and acute mania.

The compounds are effecting over a wide dosage range, the actual dose administered being dependent on such factors as the particular compound being used, the condition being treated and the type and size of mammal being treated. However, the dosage required will normally fall within the range of 0.05 to 10 mg/kg per day, for example in the treatment of adult humans dosages of from 0.2 to 5 mg/kg may be used.

The compounds and pharmaceutically-acceptable salts of the invention will normally be administered orally or by injection and, for this purpose, they will usually be utilised in the form of a pharmaceutical composition. Such compositions are prepared in a manner well known in the pharmaceutical art and normally comprise at least one active compound or pharmaceutically-acceptable carrier therefor. In making the compositions of the present invention, the active ingredient will usually be mixed with a carrier or diluted by a carrier, or enclosed with a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, manitol, starches, gum acacia, calcium phosphate, alginates, tragacanth, gelatin, syrup, methyl cellulose, methyl- and propyl-hydroxybenzoate, talc, magnesium stearate or mineral oil. The compositions of the invention may be formulated so as to provide quick, sustained or delayed release of the active ingredient after administration to the patient.

Depending on the route of administration, the foregoing compositions may be formulated as tablets, capsules or suspensions for oral use, injection solutions and subcutaneous implants. Preferably the compositions are formulated in a dosage unit form, each dosage containing from 1 to 200 or 300 mg, more usually 5 to 100 mg, of the active ingredient.

The invention is illustrated by the following Preparations and Examples.

PREPARATIONS

1-Methyl-4-pyrrolidinopiperidin-3-ene

A mixture of redistilled 1-methyl-4-piperidone (45.6 g), pyrrolidine (31.5 g) and benzene (400 ml) were refluxed over night, using a Dean-Stark water separator. The mixture was evaporated to give a dark residue which was distilled under vacuum, b.p. 115° C. at 14 mm.

3-Methyl 1,2,3,4,6,7,8,8a-octahydroisoquinol-6-one

Methylvinylketone (24.5 g) was added dropwise to 1-methyl-4-pyrrolidinopiperidin-3-ene (58 g) in dioxane, giving a slight exotherm, keeping the temperature within the range room temperature to 30° C. with cooling. After leaving at room temperature for 45 minutes the solution was refluxed for 3 hours. The mixture was hydrolysed by refluxing for 1 hour with acetic acid (30 mle, sodium acetate (16 g) and water (30 ml). The mixture was poured into ice/water, basified with NH₃ (0.880) and extracted 5 times with dichloromethane. The dichloromethane was washed with water (3 times) dried and under vacuum, b.p. 97° C. at 0.8 mm.

trans and cis-2-Methyl-1,3,4,4a,5,7,8,8a-octahydro-6(2H)-isoquinolone

2-Methyl-1,2,3,4,6,7,8,8a-octahydroisoquinol-6-one (3.30 g) in ethanol (75 ml) was hydrogenated at 60 p.s.i. in the presence of 5% Pd/C (0.5) for 2.5 hours. The catalyst was filtered off and the filtrate evaporated to give a light brown oil.

trans and cis-2-Methyl-1,2,3,4,4a,5,8,8a-octahydro-4-pyrrolidinoisoquinoline

A mixture of trans and cis-2-methyl-1,3,4,4a,5,7,8,8a-octahydro-6(2H)-isoquinolone (60 g), pyrrolidine (34.6 g) and toluene (600 ml) were refluxed over night, using a Dean and Stark Apparatus. The solution was evaporated to dryness and the residue was distilled under vacuum to give a mixture of trans and cis-2-methyl-1,2,3,4,4a,5,8,8a-octahydro-4-pyrrolidinoisoquinoline, b.p. 107° C. at 0.05 mm.

trans-2-Methyl-1,2,3,4,4a,5,8,8a-octahydro-4-pyrrolidinoisoquinoline

A mixture of trans-2-methyl-1,3,4,4a,5,7,8,8a-octahydro-6(2H)-isoquinolone (20 g), pyrrolidine (10.2 g) and toluene (200 ml) were refluxed over night, using a Dean and Stark Apparatus. The solution was evaporated to dryness and the residue was distilled under vacuum to give trans-2-methyl-1,2,3,4,4a,5,8,8a-octahydro-4-pyrrolidinoisoquinoline as a low melthing yellow solid, b.p. 106°-110° C. at 0.02 mm.

trans and cis-7-Acetyl-2-methyl-1,3,4,4a5,7,8,8a-octahydro-(2H)-isoquinolone Acetyl chloride (7.9 g) in dichloromethane (21 ml) was added dropwise at 0° C. to a stirred solution of trans and cis-2-ethyl-1,2,3,4,a,5,8,8a-octahydro-4-pyrrolidinoisoquinoline (20 g), triethylamine (13.8 g) and dichloromethane (300 ml). After stirring at room temperature for 5 hours, a solution of sodium acetate (5.3 g) in acetic acid (80 ml) and water (80 ml) was added and the mixture was stirred at room temperature over night. The mixture was basified with concentrated ammonia solution (d=0.88) and the aqueous part extracted with dichloromethane. The combined dichloromethane extracts were washed (H2O), dried (MgSO4) and evaporated to give a light brown oil which was distilled under vacuum to give trans and cis-7-acetyl-2-methyl-1,3,4,4a,5,7,8,8a-octahydro-6(2H)-isoquinolone as a light yellow oil, b.p. 90°-105° C. at 0.02 mm Hg.

Separation of trans and cis-7-acetyl-2-methyl-1,3,4,4a,5,7,8,8a-octahydro-6(2H)-isoquinolone isomers The isomers (7.8 g) were dissolved in a mixture of solvents consisting of 10% methanol and 0.4% concentrated ammonia solution (d=0.88) in dichloromethane (50 ml) then separated using a preparatory liquid chromatography system (Waters Associates Prep. LC/System 500 Liquid Chromatograph and a Prep PAK-500/silica cartridge) eluting with the above mixture of solvents.

Evaporation of the appropriate fractions yielded, first, cis-7-acetyl-2-methyl-1,3,4,4a,5,7,8,8a-octahydro-6(2H)-isoquinolone as a pale yellow oily solid and, second, trans-7-acetyl-2-methyl-1,3,4,4a,5,7,8,8a-octahydro-6(2H)-isoquinolone as a pale yellow oily solid.

trans-7-Acetyl-2-methyl-1,3,4,4a,5,7,8,8a-octahydro-6(2H)-isoquinolone trans-2-Methyl-1,3,4,4a,5,7,8,8a-octahydro-6(2H)-isoquinolone (10 g) in tetrahydrofuran (10 ml) was added to a stirred mixture of 50% sodium hydride oil dispersion (5.8 g) in tetrahydrafuran (100 ml) at room temperature. After 1 hour, ethanol (3.44 ml) in tetrahydrofuran (10 ml) was added at room temperature for 1.5 hours. After cooling to 10°, a solution of ethylacetate (17.6 ml) in tetrahydrofuran (20 ml) was added and the reaction mixture was heated at 50° C. over the weekend. Following the addition of water the mixture was acidified (5N HCl) and extracted with ether. The aqueous part was basified with concentrated ammonia solution (d=0.88) and extracted with dichloromethane three times. The dichloromethane extracts were washed (H2O), dried (MgSO4) and evaporated to give a brown oil which was distilled under vacuum to give trans-7-acetyl-2-methyl-1,3,4,4a,5,7,8,8a-octahydro-6(2H)-isoquinolone as a light yellow solid, b.p. 95°-102° C. at 0.02 mm.

Similarly prepared were:

trans-2-Methyl-1,3,4,4a,5,7,8,8a-octahydro-7-propionyl-6(2H)-isoquinolone, b.p. 120°-135° C. at 0.03 mm trans-7-Butyryl-2-methyl-1,3,4,4a,5,7,8,8a-octahydro-6(2H)-isoquinolone, b.p. 118° C. at 0.02 mm trans-7-Isobutyryl-2-methyl-1,3,4,4a,5,7,8,8a-octahydro-6(2H)-isoquinolone, b.p. 80°-90° C. at 0.02 mm trans-7-Methyl-1,3,4,4a,5,7,8,8a-octahydro-7-valeryl-6(2H)-isoquinolone, b.p. 125° C. at 0.05 mm.

trans-7-Hexanoyl-2-methyl-1,3,4,4a,5,7,8,8a-octahydro-6(2H)-isoquinolone, b.p. 71°-76° C. at 0.04 mm trans-7-Heptanoyl-2-methyl-1,3,4,4a,5,7,8,8a-octahydro-6(2H)-isoquinolone, b.p. 65°-75° C. at 0.02 mm trans-2-Methyl-1,3,4,4a,5,7,8,8a-octahydro-7-trimethylacetyl-6(2H)-isoquinolone, b.p. 80° C. at 0.04 mm trans-7-Cyclopentylcarbonyl-2-methyl-1,3,4,4a,5,7,8,8a-octahydro-6(2H)-isoquinolone, b.p. 124°-125° C. at 0.01 mm trans-7-Cyclopropylacetyl-2-methyl-1,3,4,4a,5,7,8,8a-octahydro-6(2H)-isoquinolone trans-7-Benzoyl-2-methyl-1,3,4,4a,5,7,8,8a-octahydro-6(2H)-isoquinolone trans-2-Methyl-1,3,4,4a,5,7,8,8a-octahydro-7-phenylacetyl-6(2H)-isoquinolone, b.p. 155°-165° C. at 0.01 mm cis-2-Methyl-1,3,4,4a,5,7,8,8a-octahydro-7-propionyl-6(2H)-isoquinolone, b.p. 86°-100° C. at 0.03 mm cis-7-Butyryl-2-methyl-1,3,4,4a,5,7,8,8a-octahydro-6(2H)-isoquinolone, b.p. 90°-95° C. at 0.02 mm cis-7-Isobutyryl-2-methyl-1,3,4,4a,5,7,8,8a-octahydro-6(2H)-isoquinolone, b.bp. 110° C. at 0.02 mm cis-2-Methyl-1,3,4,4a,5,7,8,8a-octahydro-7-valeryl-6(2H)-isoquinolone, b.p. 90°-100° C. at 0.05 mm cis-7-Benzoyl-2-methyl-1,3,4,4a,5,7,8,8a-octahydro-6(2H)isoquinolone

Resolution of trans-2-methyl-1,3,4,4a,5,7,8,8a-octahydro-6(2H)-isoquinolone trans-2-Methyl-1,3,4,4a,5,7,8,8a-octahydro-6(2H)-isoquinolone (12.7 g) was added at room temperature to (−)-di-p-toluoyl-L-tartaric acid monohydrate, 97% (25 g) dissolved in methanol (220 ml). The precipitated tartrate was recrystallised twice from methanol, ($[\alpha]_D^{26}$=−103°, C=1.09% in MeOH).

The free base was liberated with ammonium hydroxide, isolated by dichloromethane extraction and distilled bulb to bulb under vacuum to give (−)-trans-2-methyl-1,3,4,4a,5,7,8,8a-octahydro-6(2H)-isoquinolone as a colourless oil, b.p. 65° C. at 0.6 mm, ($[\alpha]_D^{22}$=−60.7°, C=1.2%, CH2Cl2).

The filtrate from the original tartrate precipitation was converted to the free base with ammonium hydroxide and collected by dichloromethane extraction followed by evaporation. The crude oil (6.9 g) thus obtained was added to (+)-Di-p-toluoyl-D-tartaric acid monohydrate, 97% (13.6 g) dissolved in methanol (120 ml) at room temperature. The precipitated tartrate was recrystallised twice from methanol, ($[\alpha]_D^{26}$=+103, c=0.98% in MeOH). The free base was liberated with ammonium hydroxide, isolated by dichloromethane extraction and distilled bulb to bulb under vacuum to give (+)-trans-2-methyl-1,3,4,4a,5,7,8,8a-octahydro-6(2H)-isoquinolone as a colourless oil, b.p. 66° at 0.6 mm, ([α]$_D^{22}$=+57.3°, C=0.91%, CH$_2$Cl$_2$).

Similarly prepared were:

trans-7-Acetyl-1,3,4,4a,5,7,8,8a-octahydro-2-propyl-6(2H)-isoquinolone b.p. 140° C. at 0.01 mmHg.

trans-1,3,4,4a,5,7,8,8a-Octahydro-7-propionyl-2-propyl-6(2H)-isoquinolone trans-7-Acetyl-2-methylethyl-1,3,4,4a,5,7,8,8a-octahydro-6(2H)-isoquinolone 7-Dimethylaminomethylene-2-methyl-1,2,3,4,4a,5,8,8a-octahydro-6(2H)-isoquinolone 2-Methyl-1,3,4,4a,5,7,8,8a-octahydro-6(2H)-isoquinolone (10 g) and tert-butoxy-bis-(dimethylamino) methane (12.5 g) were heated together at 50° C. for 18 hours. Excess reagent was removed by evaporation and the residue subjected to short path distillation in vacuo to give the title compound as an oily solid, b.p. 80° C. at 0.1 mm.

EXAMPLE 1 trans-6-Methyl-4,4a,5,6,7,8,8a,9-octahydro-1H-pyrazolo[3,4-g]isoquinolone

To a solution of 7-dimethylaminomethylene-2-methyl-1,2,3,4,4a,5,8,8a-octahydro-6(2H)-isoquinolone (6.7 g) in methanol (60 ml) was added a solution of hydrazine (1.06 g) in methanol (10 ml). The mixture was refluxed over night and evaporated in vacuo to an oil. Chromatography on neutral alumina using dichloromethane -methanol gave the title compound, m.p. 245°–247° C. (as hemifumarate salt).

EXAMPLE 2 trans-3,6-Dimethyl-4,4a,5,6,7,8,8a,9-octahydro-1H-pyrazolo[3,4-g]isoquinoline

To a solution of trans-7-acetyl-2-methyl-1,3,4,4a,5,7,8,8a-octahydro-6(2H)-isoquinolinone (15.8 g) in methanol (10 ml) was added a solution of hydrazine (5 ml) in methanol (10 ml). The solution was stirred for 48 hours and evaporated to dryness. Chromatography on silica gel using 5% ethanol in chloroform gave the title compound, m.p. 160°–162° C. (cyclohexane).

Similarly prepared were (−)trans-3,6-Dimethyl-4,4a,5,6,7,8,8a,9-octahydro-1H-pyrazolo[3,4-g]isoquinoline from (−)trans-7-acetyl-2-methyl-1,3,4,4a,5,7,8,8a-octahydro-6(2H)-isoquinolinone, m.p. 282°–288° C. (as dihydrochloride salt)

(+)trans-3,6-Dimethyl-4,4a,5,6,7,8,8a,9-octahydro-1H-pyrazolo[3,4-g]isoquinoline from (+)trans-7-acetyl-2-methyl-1,3,4,4a,5,7,8,8a-octahydro-6(2H)-isoquinolinone, m.p. 283°–284° C. (as dehydrochloride salt)

trans-3-Ethyl-6-methyl-4,4a,5,6,7,8,8a,9-octahydro-1H-pyrazolo[3,4-g]isoquinoline from trans-2-methyl-1,3,4,4a,5,7,8,8a-octahydro-7-propionyl-6(2H)-isoquinolinone (as a non-crystalline hygroscopic dihydrochloride salt).

trans-6-Methyl-4,4a,5,7,7,8,8a,9-octahydro-3-propyl-1H-pyrazolo[3,4-g]isoquinoline from trans-7-butyryl-2-methyl-1,3,4,4a,5,7,8,8a-octahydro-6(2H)-isoquinolinone, m.p. 140°–146° C. (as dihydrochloride salt).

trans-6-Methyl-3-methylethyl-4,4a,5,6,7,8,8a,9-octahydro-1H-pyrazolo[3,4 g]isoquinoline from trans-7-isobutyryl-2-methyl-1,3,4,4a,5,7,8,8a-octahydro-6(2H)-isoquinolinone, m.p. 173°–177° C. (as dihydrochloride salt).

trans-3-Butyl-6-methyl-4,4a,5,6,7,8,8a,9-octahydro-1H-pyrazolo[3,4-g]isoquinoline from trans-2-methyl-1,3,4,4a,5,7,8,8a-octahydro-7-valeryl-6(2H)-isoquinolinone (as a non-crystalline hygroscopic dihydrochloride salt).

trans-3-t-Butyl-6-methyl-4,4a,5,6,7,8,8a,9-octahydro-1H-pyrazolo[3,4-g]isoquinoline from trans-2-methyl-1,3,4,4a,5,7,8,8a octahydro-7-trimethylacetyl-6(2H)-isoquinolinone, m.p. 193°–195° C. (as dihydrochloride salt).

trans-6-Methyl-4,4a,5,6,7,8,8a,9-octahydro-3-pentyl-1H-pyrazolo[3,4-g]isoquinoline from trans-7-hexanoyl-2-methyl-1,3,4,4a,5,7,8,8a-octahydro-6(2H)-isoquinolinone, m.p. 185°–191° C. (as sesquifumarate salt).

trans-3-Cyclopentyl-6-methyl-4,4a,5,6,7,8,8a,9-octahydro-1H-pyrazolo[3,4-g]isoquinoline from trans-7-cyclopentylcarbonyl-2-methyl-1,3,4,4a,5,7,8,8a-octahydro-6(2H)-isoquinolinone, m.p. 196°–200° C. (as hydrochloride salt).

trans-3-Hexyl-6-methyl-4,4a,5,6,7,8,8a,9-octahydro-1H-pyrazolo[3,4-g]isoquinoline from trans-7-heptanoyl-2-methyl-1,3,4,4a,5,7,8,8a-octahydro-6(2H)-isoquinolinone (as a non-crystalline, hygroscopic dihydrochloride salt).

trans-3-cyclopropylmethyl-6-methyl-4,4a,5,6,7,8,8a,9-octahydro-1H-pyrazolo[3,4-g]isoquinoline from trans-7-cyclopropylacetyl-2-methyl-1,3,4,4a,5,7,8,8a-octahydro-6(2H)-isoquinolinone, m.p. 181°–184° C. (as sesquifumarate salt).

trans-3-Benzyl-6-methyl-4,4a,5,6,7,8,8a,9-octahydro-1H-pyrazolo[3,4-g]isoquinoline from trans-2-methyl-7-phenylacetyl-1,3,4,4a,5,7,8,8a-octahydro-6(2H)-isoquinolinone, m.p. 205°–209° C. (as sesquifumarate salt).

trans-6-Methyl-3-phenyl-4,4a,5,6,7,8,8a,9-octahydro-1H-pyrazolo[3,4-g]isoquinoline from trans-7-benzoyl-2-methyl-1,3,4,4a,5,7,8,8a-octahydro-6(2H)-isoquinolinone, m.p. 269°–274° C. (as dihydrochloride salt).

trans-3-Methyl-6-propyl-4,4a,5,6,7,8,8a,9-octahydro-1H-pyrazolo[3,4-g]isoquinoline from trans-7-acetyl-2-propyl-1,3,4,4a,5,7,8,8a-octahydro-6(2H)-isoquinolinone, m.p. 220°–224° C. (as dihydrochloride salt).

trans-3,6-Dipropyl-4,4a,5,6,7,8,8a,9-octahydro-1H-pyrazolo[3,4-g]isoquinoline from trans-7-butyryl-2-propyl-1,3,4,4a,5,7,8,8a-octahydro-6(2H)-isoquinolinone, m.p. 220°–230° C. (as dihydrochloride salt).

trans-6-Methylethyl-3-methyl-4,4a,5,6,7,8,8a,9-octahydro-1H-pyrazolo[3,4-g]isoquinoline from trans-7-acetyl-2-isopropyl-1,3,4,4a,5,7,8,8a-octahydro-6(2H)-isoquinolinone, m.p. 270°–273° C. (as dihydrochloride salt).

cis-3,6-Dimethyl-4,4a,5,6,7,8,8a,9-octahydro-1H-pyrazolo[3,4-g]isoquinoline from cis-7-acetyl-2-methyl-1,3,4,4a,5,7,8,8a -octahydro-6(2H)-isoquinolinone, m.p. 185°–187° C. (as dihydrochloride salt).

cis-3-Ethyl-6-methyl-4,4a,5,6,7,8,8a,9-octahydro-1H-pyrazolo[3,4-g]isoquinoline from cis-2-methyl-7-propionyl-1,3,4,4a,5,7,8,8a-octahydro-6(2H)isoquinolinone, m.p. 195°–200° C. (as dihydrochloirde salt).

cis-6-Methyl-3-propyl-4,4a,5,6,7,8,8a,9-octahydro-1H-pyrazolo[3,4-g]isoquinoline from cis-7-butyryl-2-methyl-1,3,4,4a,5,7,8,8a-octahydro-6(2H)isoquinolinone, m.p. 170°–176° C. (as dihydrochloride salt).

cis-6-Methyl-3-methylethyl-4,4a,5,6,7,8,8a,9-octahydro-1H-pyrazolo[3,4-g]isoquinoline from cis-7-isobutyryl-2-methyl-1,3,4,4a,5,7,8,8a-octahydro-6(2H)-isoquinolinone, m.p. 188°–194° C. (as dihydrochloride salt).

cis-3-Butyl-6-methyl-4,4a,5,6,7,8,8a,9-octahydro-1H-pyrazolo[3,4-g]isoquinoline from cis-2-methyl-7-valeryl-1,3,4,4a,5,7,8,8a-octahydro-6(2H)-isoquinolinone, m.p. 172°–176° C. (as dihydrochloride salt).

cis-6-Methyl-3-pheyl-4,4a,5,6,7,8,8a,9-octahydro-1H-pyrazolo[3,4-g]isoquinoline from cis-7-benzoyl-2-methyl-1,3,4,4a,5,7,8,8a-octahydro-6(2H)-isoquinolinone, m.p. 203°–211° C. (as hemifumarate salt).

EXAMPLE 3 trans-4,4a,5,6,7,8,8a,9-Octahydro-1,3,6-trimethyl-1H-pyrazolo[3,4-g]isoquinoline and
trans-4,4a,5,6,7,8,8a,9-octahydro-2,3,6-trimethyl-1H-pyrazolo[3,4-g]isoquinoline A solution of methylhydrazine (0.66 g) in methanol (2 ml) was added dropwise at room temperature to a solution of trans-7-acetyl-2-methyl-1,3,4,4a,5,7,8,8a-octahydro-6(2H)isoquinolone (2.51 g) in methanol (10 ml) and stirred for 24 hours. The solution was evaporated to dryness and the two isomers formed in the reaction separated using a Waters Associates Prep LC/system 500 liquid (homotograph and a Prep PAK-500/silica cartridge with dichloromethane: methanol: ammonia (80:10:0.4) as elution solvent. Collection of appropriate fractions gave the title compounds, trans-4,4a,5,6,7,8,8a,9-octahydro-1,3,6-trimethyl-1H-pyrazolo[3,4-g]isoquinoline, m.p. 159°–165° C. (as dihydrochloride salt) and trans -4,4a,5,6,7,8,8a,9-octahydro-2,3,6-trimethyl-1H-pyrazolo[3,4-g]isoquinoline, m.p. 220°–230° C. (as dihydrochloride salt).

EXAMPLE 4 trans-6-Methyl-3-propylthio-4,4a,5,6,7,8,8a,9-octahydro-1H-pyrazolo[3,4-g]isoquinoline To a stirred solution of potassium tertiary butoxide (2.5 g) in dry tetrahydrofuran (50 ml) under nitrogen was added, sequentially trans-2-methyl-1,3,4,4a,5,7,8,8a-octahydro-6(2H)-isoquinolone (2 g) and carbon disulphide (0.76 ml). The brick-red precipitate was stirred with ice cooling and 1-iodopropane (2.6 ml) added dropwise. The mixture was stirred with ice cooling for 30 minutes and at ambient temperature for 1 hour. The mixture was poured into ice-water, extracted into methylene chloride (2×25 ml) washed with water and dried over magnesium sulphate. After evaporation of the solvent the crude intermediate was dissolved in ethanol (25 ml) hydrazine hydrate (1 ml) was added and mixture heated under nitrogen at 60° C. for 2 hours. After evaporation of the solvent the residue was partitioned between diethyl ether and dilute hydrochloric acid. The aqueous phase was basified with sodium carbonate solution and extracted into methylene chloride. After drying over magnesium sulphate and stripping of the solvent the residue was chromatographed on silica gel eluting with 0 to 5% methanol in chloroform, followed by crystallisation from acetonitrile, m.p. 127° C.

Similarly prepared were
trans-6-Methyl-3-methylthio-4,4a,5,6,7,8,8a,9-octahydro-1H-pyrazolo[3,4-g]isoquinoline, m.p. 157°–164° C. (sublimes) (from acetonitrile)

trans-6-Methyl-3-(1-methylethyl)thio-4,4a,5,6,7,8,8a,9-octahydro-1H-pyrazolo[3,4-g]isoquinoline, m.p. 167° C. (from acetonitrile)

trans-2,6-Dimethyl-3-methylthio-4,4a,5,6,7,8,8a,9-octahydro-2H-pyrazolo[3,4-g]isoquinoline, m.p. 81° C. (from acetonitrile).

trans-3-Methylthio-6-propyl-4,4a,5,6,7,8,8a,9-octahydro-1H-pyrazolo[3,4-g]isoquinoline from trans-2-propyl-1,3,4,4a,5,7,8,8a-octahydro-6(2H)isoquinolone, m.p. 64°–66° C. (from EtOAc/hexane).

trans-6-(1-Methylethyl)-3-methylthio-4,4a,5,6,7,8,8a,9-octahydro-1H-pyrazolo[3,6-g]isoquinoline from trans-2-(1-methylethyl-1,3,4,4a,5,7,8,8a-octahydro-6(2H)isoqinoline, m.p. 78°–80° C. (from acetonitrile).

The following Examples illustrate the preparation of typical formulations containing a solid active ingredient according to the invention.

EXAMPLE 5

Hard gelatin capsule

Each capsule contains

| Active ingredient | 10 mg |
|---|---|
| PEG 4000 | 250 mg |

The PEG 4000 is melted and mixed with the active ingredient. Whilst still molten the mixture is filled into capsule shells and allowed to cool.

EXAMPLE 6

Tablet

Each tablet contains

| Active ingredient | 10 mg |
|---|---|
| Calcium carbonate | 300 mg |
| Magnesium stearate | 10 mg |
| Starch | 30 mg |
| Hydroxypropylmethyl-cellulose | 10 mg |
| Iron Oxide | 4 mg |

The active ingredient is granulated with calcium carbonate and starch. The dried granulate is blended with lubricant and disintegrant and compressed into tablets of the required dosage strength. The tablet may then be coated.

EXAMPLE 7

Injection

| Active ingredient | 10 mg |
|---|---|
| Water | 1 mg |

The active is dissolved in water and distributed into vials, ampoules or pre-pack syringes using appropriate equipment. The product is sterilised.

EXAMPLE 8

Controlled-Release Injection

| Active ingredient | 50 mg |
|---|---|
| Arachis oil | 2 ml |

The active is dissolved in the oil and distributed into vials, ampoules or pre-pack syringes. The product is sterilised.

EXAMPLE 9

Subcutaneous Implant

| Active ingredient | 250 mg |
|---|---|
| Poly (ε-caprolactone) | 4.75 g |

A solution of the active in a suitable solvent is added to the polymer, the mass moulded into appropriately-shaped dosage units. Solvent is evaporated and the product sterilised.

We claim:

1. A compound of the formula

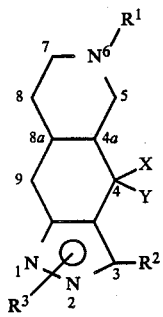

(I)

in which $R^1$ is hydrogen or $C_{1-6}$ alkyl, $R^2$ is hydrogen, $C_{1-6}$ alkyl optionally substituted by $C_{3-9}$ cycloalkyl or optionally substituted phenyl, $C_{3-9}$ cycloalkyl, optionally substituted phenyl, or $-SR^4$ where $R^4$ is $C_{1-6}$ alkyl optionally substituted by $C_{3-9}$ cycloalkyl or optionally substituted phenyl, or $C_{3-9}$ cycloalkyl, $R^3$ is hydrogen, $C_{1-6}$ alkyl optionally substituted by $C_{3-9}$ cycloalkyl or optionally substituted phenyl, $C_{3-9}$ cycloalkyl, or optionally substituted phenyl, and either X and Y are both hydrogen or together are =O; or a pharmaceutically-acceptable acid addition salt thereof.

2. A compound according to claim 1 in which $R^1$ is $C_{1-4}$ alkyl, $R^2$ is hydrogen, $C_{1-4}$ alkyl or $C_{3-9}$ cycloalkyl, $R^3$ is hydrogen or $C_{1-4}$ alkyl and $R^4$ is $C_{1-4}$ alkyl.

3. A compound according to claim 2 in which X and Y are both hydrogen.

4. A compound of the formula

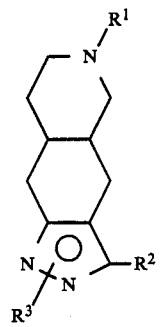

in which $R^1$ is $C_{1-4}$ alkyl, $R^2$ is $C_{1-4}$ alkyl optionally substituted by cyclopropyl, or $-SR^4$ where $R^4$ is $C_{1-4}$ alkyl, and $R^3$ is hydrogen; or a pharmaceutically-acceptable acid addition salt thereof.

5. A compound according to claim 4 in which the 4a,8a ring junction is trans.

6. A pharmaceutical composition comprising a compound according to claim 1, or a pharmaceutically-acceptable acid addition salt thereof, together with a pharmaceutically-acceptable diluent or carrier therefor.

7. A method of treating an animal suffering from a disorder of the central nervous system, which comprises administering an effective amount of a compound of formula (I) as defined in claim 1, or a pharmaceutically-acceptable salt thereof.

* * * * *